(12) United States Patent  (10) Patent No.: US 7,528,608 B2
Elexpuru et al.  (45) Date of Patent: May 5, 2009

(54) SENSOR DEVICE FOR A HOUSEHOLD APPLIANCE

(75) Inventors: Antón Elexpuru, Mondragón (ES); Jose Ignacio Oñate, Plentzia (ES)

(73) Assignee: Coprecitec, S.L., Aretxabaleta (Guipuzkoa) (ES)

( * ) Notice: Subject to any disclaimer, the term of this patent is extended or adjusted under 35 U.S.C. 154(b) by 245 days.

(21) Appl. No.: 11/717,886

(22) Filed: Mar. 14, 2007

(65) Prior Publication Data

US 2007/0236226 A1     Oct. 11, 2007

(30) Foreign Application Priority Data

Apr. 7, 2006   (EP) ................... 06380070

(51) Int. Cl.
*G01R 27/22* (2006.01)
(52) U.S. Cl. .............. 324/445; 324/511; 324/510; 324/439
(58) Field of Classification Search ............ 324/510, 324/511, 439; 68/12.02
See application file for complete search history.

(56) References Cited

U.S. PATENT DOCUMENTS

2004/0143994 A1* 7/2004 Baron et al. ............... 34/597
2005/0081572 A1  4/2005 Park et al.
2005/0174123 A1  8/2005 Ott

FOREIGN PATENT DOCUMENTS

WO   WO2005061775 A1   7/2005

* cited by examiner

*Primary Examiner*—Vincent Q Nguyen
(74) *Attorney, Agent, or Firm*—Peter B. Scull; Berenbaum Weinshienk & Eason; Tim L. Kitchen

(57) ABSTRACT

Sensor device for a household appliance that includes a body (2), detector device to measure at least one variable of a fluid and which includes a conductivity sensor, and a printed circuit (3) that receives the variables measured by the detector device. The body (2) includes a housing (20) where the printed circuit (3) is housed, and the device (1) also includes a cover (6) to close the housing (20). The body (2) also includes an inlet conduit (21) and an outlet conduit (22) through which said fluid passes, the housing (20), the printed circuit (3) and the cover (6) being disposed transversally to the conduits (21, 22) between the conduits (21, 22). The conductivity sensor is connected to said body (2) and is connected to or next to the printed circuit (3).

13 Claims, 5 Drawing Sheets

SENSOR DEVICE FOR A HOUSEHOLD APPLIANCE

TECHNICAL FIELD

The present invention relates to sensor devices used to measure at least one variable of a fluid used in household appliances.

PRIOR ART

In household appliances of the dishwasher or washing machine type, for example, it is important to control certain variables of the water or fluid they use to achieve suitable control of their operation. These variables can be, for example, the turbidity (or transparency), temperature or conductivity of said fluid.

Sensor devices are known that comprise detector means to measure at least one of the aforementioned variables, such as documents US 2005/0081572 A1 and US 2005/0174123 A1, which disclose a device with a conductivity sensor to measure the conductivity of the water or fluid used by the household appliance where said device is disposed.

WO 2005/061775 A1 also discloses a device with detector means to measure at least one variable of the water or fluid used by the household appliance where said device is disposed, said detector means comprising a conductivity sensor to measure the conductivity of said fluid. Said device comprises a longitudinal body that delimits a housing where a printed circuit is disposed, and a cover that is disposed on said printed circuit insulating said printed circuit from the exterior and closing said housing, therefore closing said body.

DISCLOSURE OF THE INVENTION

It is an object of this invention to provide a sensor device to measure at least one variable of a fluid used in a household appliance, as described in the claims.

The sensor device of the invention, used in a household appliance, comprises a body, detector means to measure at least one variable of a fluid which comprise a conductivity sensor, and a printed circuit that receives the variables measured by the detector means. The body comprises a housing where said printed circuit is housed, and the device also comprises a cover to close said housing.

The body also comprises an inlet conduit and an outlet conduit through which passes the fluid whose variables are to be measured. The housing, the printed circuit and the cover are disposed transversally to said conduits and between said conduits.

In this way, the printed circuit can be disposed in the housing and the cover can close said housing in a simple way, thereby enabling the detector means to measure the variables of the fluid longitudinally in relation to the flow of said fluid.

As the printed circuit is disposed in the housing and as said housing is comprised between the inlet conduit and the outlet conduit, the conductivity sensor can easily be joined to the body to measure the variables of the fluid that passes through said conduits, with said conductivity sensor being connected to or next to the printed circuit.

These and other advantages and characteristics of the invention will be made evident in the light of the drawings and the detailed description thereof.

DETAILED DISCLOSURE OF THE INVENTION

Figure 1:
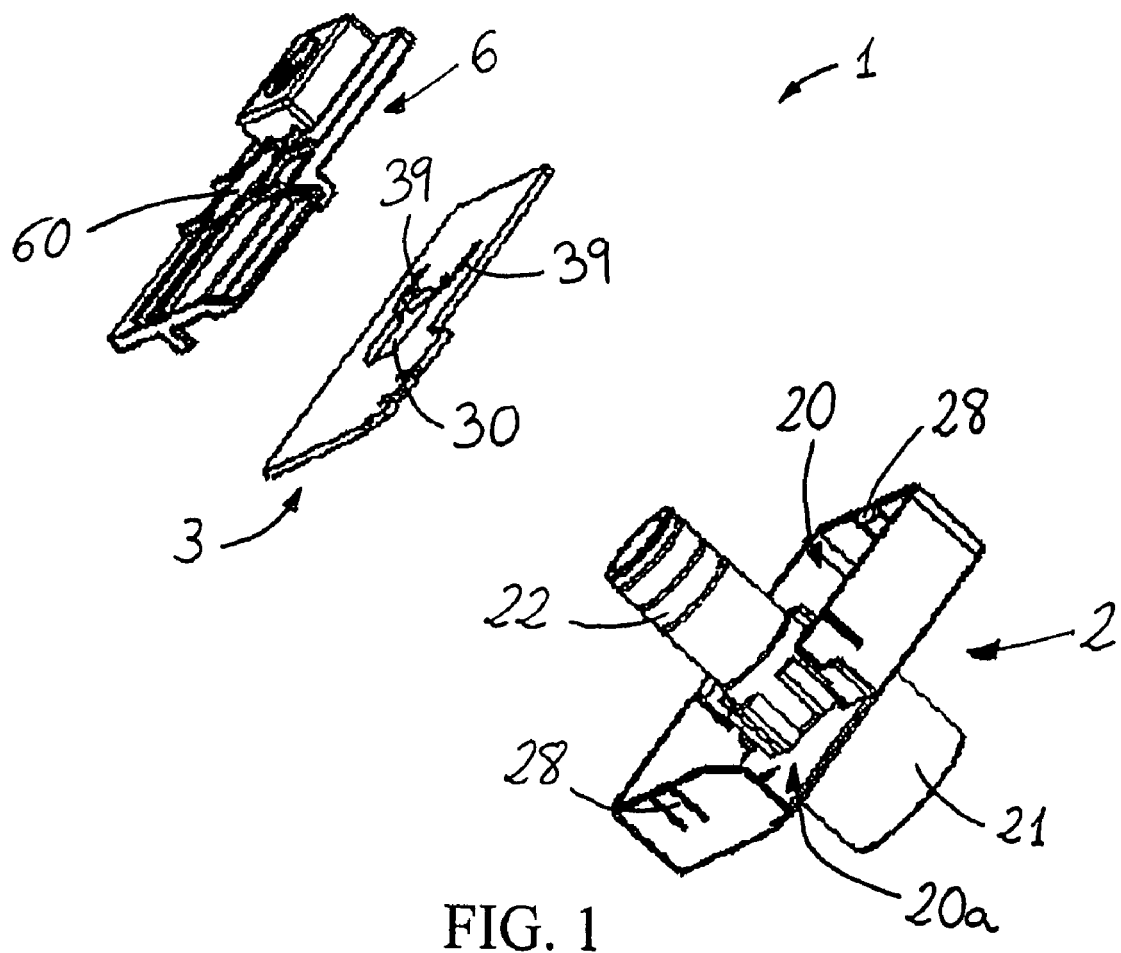
FIG. 1 is an exploded view of an embodiment of the device of the invention.
Figure 2:
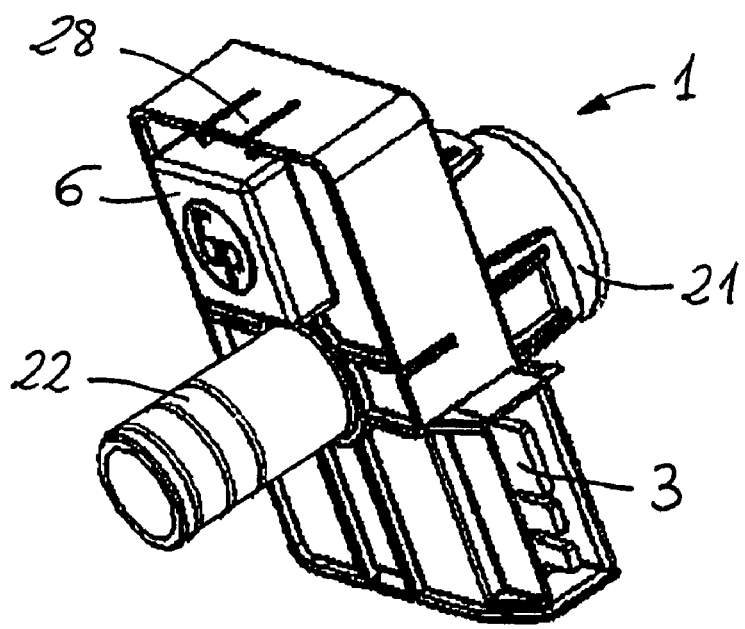
FIG. 2 is a perspective view of the device of FIG. 1.

FIGS. 1 and 2 show an embodiment of the sensor device 1 of the invention, used generally in a household appliance of the washing machine or dishwasher type (not shown in the figures). The device 1 comprises a body 2 that can be made of injected plastic, detector means to measure at least one variable of a fluid and which comprise a conductivity sensor, and a printed circuit 3 that receives the variables measured by the detector means.

The body 2 comprises a housing 20 where the printed circuit 3 is housed, said housing 20 comprising fastening means 29 that are housed in grooves 39 of said printed circuit 3, said printed circuit 3 being held in said housing 20. The device 1 comprises a cover 6 to close said housing 20, said housing 20 comprising fixing means 28, such as, for example, tabs, in order to fix said cover 6 to said housing 20.

The body 2 also comprises an inlet conduit 21 and an outlet conduit 22, generally open, through which passes the fluid whose variables are measured, with said housing 20, said printed circuit 3 and said cover 6 being disposed between said conduits 21 and 22, transversally to said conduits 21 and 22. Said housing 20 comprises a window 20a through which the printed circuit 3 is connected to wherever necessary.

The device 1 can be positioned, for example, in the entrance to the general water intake measuring at least one variable of said water, in the circulation circuit of a fluid used in the household appliance where said device 1 is disposed, measuring at least one variable of said fluid, and/or in the evacuation circuit of said fluid, measuring at least one variable of said evacuated fluid. As said device 1 comprises an open inlet conduit 21 and an open outlet conduit 22, it is adapted to be disposed in any of said positions in series with the flow of said fluid, or either in well closing said outlet conduit 22.

Figure 3:
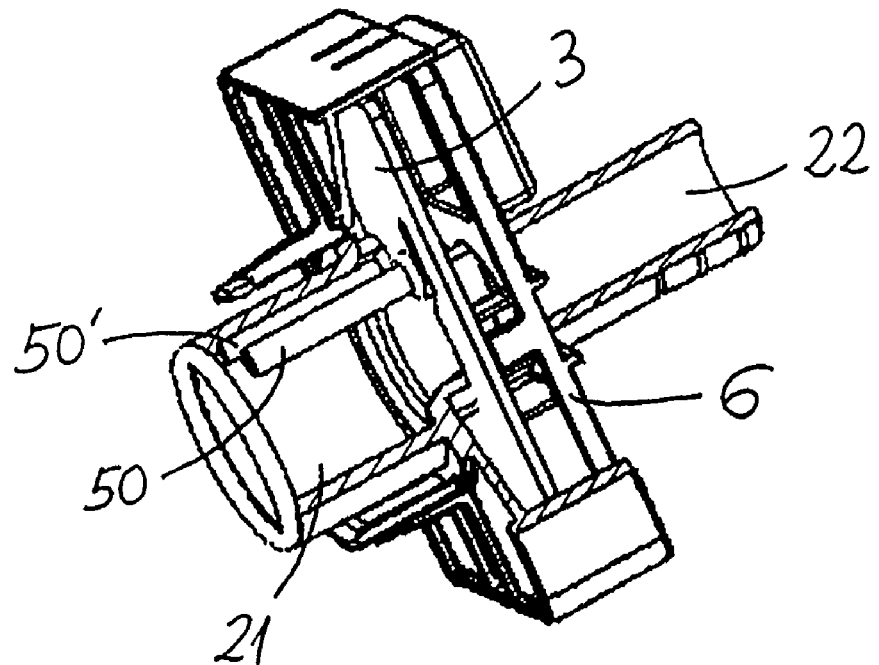
FIG. 3 is a perspective view of a first embodiment of the device of FIG. 1, showing the electrodes.

The conductivity sensor is connected to the body 2, and is connected to or next to the printed circuit 3, being capable of measuring the conductivity of the fluid that passes through the inlet conduit 21 or the outlet conduit 22. In a first embodiment shown in FIG. 3, said conductivity sensor comprises two electrodes 50 and 50' that extend longitudinally and in parallel in one of the conduits 21, 22 of said body 2, being capable of measuring the conductivity of the fluid as it passes through said conduit 21, 22. Said electrodes 50 and 50' are connected to said printed circuit 3 so that said printed circuit 3 receives the measurements obtained by said electrodes 50 and 50'. Said conduit 21, 22 is the inlet conduit 21, and said electrodes 50 and 50' are disposed in respective longitudinal grooves (not shown in the figures) of said inlet conduit 21, said electrodes 50 and 50' being disposed, therefore, longitudinal to the flow of the fluid that passes through said inlet conduit 21.

Said longitudinal grooves comprise respective parallel stoppers (not shown in the figures) so that as said electrodes 50 and 50' are disposed in said longitudinal grooves, the two electrodes 50 and 50' extend towards a same length in said inlet conduit 21.

Figure 4:
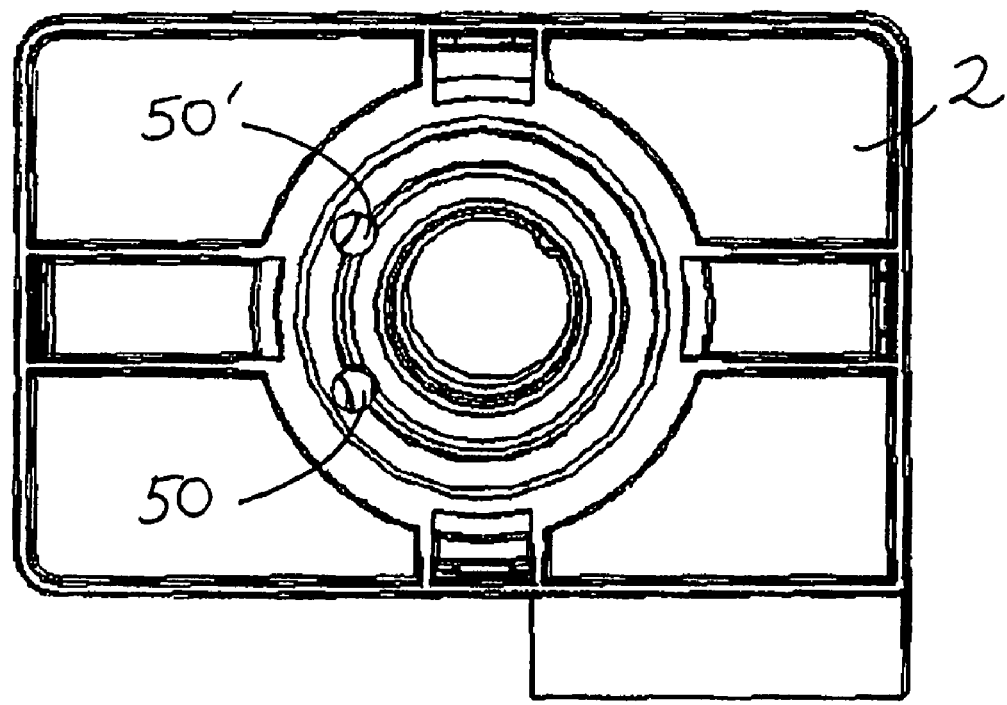
FIG. 4 is a ground view of the first embodiment of the device of FIG. 1, with the electrodes in a certain position.

The body 2 also comprises fixing means disposed on one of the conduits 21 and 22 which comprise, for example, a flexible tab (not shown in the figures) that cooperates with a housing (not shown in the figures) disposed on said conduit 21, 22, so that the electrodes 50 and 50' are disposed in a certain position in relation to the flow of the fluid shown in FIG. 4. In said certain position said electrodes 50 and 50' prevent the depositing of particles that may alter the measurements, and can also be continually submerged in the fluid thereby preventing the oxidation process, or can also be exposed to the air in controlled time periods to obtain the required measurements.

Figure 5:
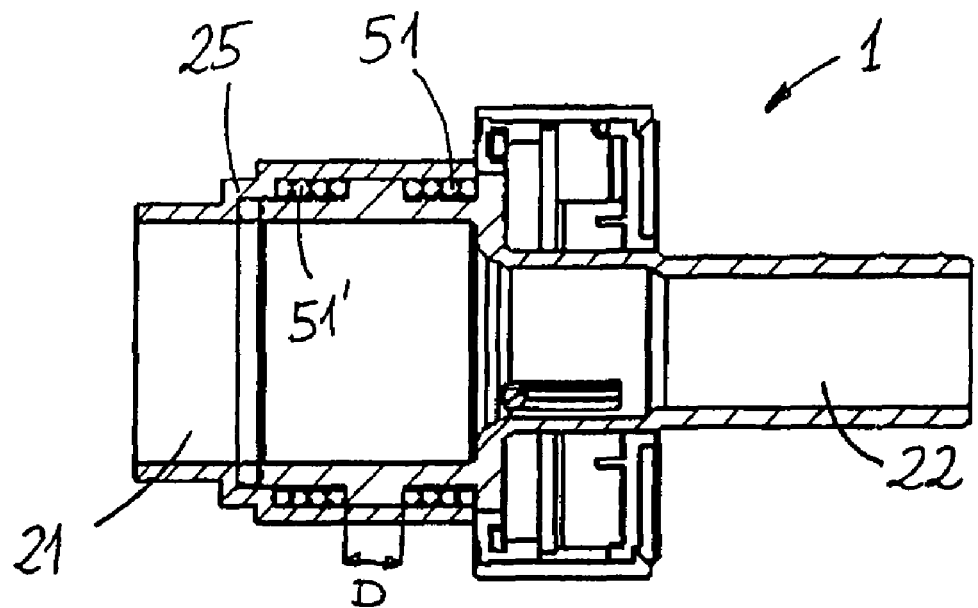
FIG. 5 is a section view of a second embodiment of device of FIG. 1.

In a second embodiment shown in FIG. 5, the conductivity sensor comprises two inductive conductors 51 and 51' rolled up in one of the conduits 21, 22, said conductors 51 and 51' being disposed next to the printed circuit 3. Said conduit 21, 22 is the inlet conduit 21, and said conductors 51 and 51' are disposed in respective ring-shaped grooves (not shown in the figures) that said inlet conduit 21 has on its outer surface (although they can also be disposed on the inner surface), said ring-shaped grooves being parallel and separated from each other by a certain distance D. The body 2 comprises insulation means 25 disposed on said inlet conduit 21 and concentric to said inlet conduit 21 so that said conductors 51 and 51' are insulated from the exterior, thereby preventing external magnetic fields from affecting the measurements taken by said conductors 51 and 51'.

Preferably, the housing 20 delimits an area around the outlet conduit 22 of the body 2, although it can also delimit an area around the inlet conduit 21. The printed circuit 3 is disposed on said area, with said printed circuit 3 and the cover 6 comprising cavities 30 and 60 respectively that are crossed by said outlet conduit 22. In this way, in the first embodiment, said housing 20 comprises a through hole 20b, shown in FIG. 6, for each electrode 50, 50', said electrodes 50 and 50' capable of being connected to said printed circuit 3.

The detector means also comprise a turbidity sensor to measure the turbidity of the fluid that passes through the outlet conduit 22, although they can also measure the turbidity of said fluid as it passes through the inlet conduit 21. Said turbidity sensor comprises a light emitter (not shown in the figures) and at least one light receiver (not shown in the figures) disposed on the printed circuit 3. Said light emitter emits a beam of light that after passing through said outlet conduit 22, and therefore the fluid that passes through said outlet conduit 22, is received by the light receiver, thereby determining the turbidity or transparency of said fluid in accordance with said light received by said light receiver. The light receiver is disposed on the printed circuit 3 so that it receives the beam of light emitted by said light emitter in a direct manner. Said turbidity sensor may also comprise a second light receiver (not shown in the figures) disposed on said printed circuit 3 so that it receives the beam of light emitted by said light emitter perpendicularly, the turbidity or transparency of said fluid being obtained in accordance with the light received by both receivers.

Figure 6:
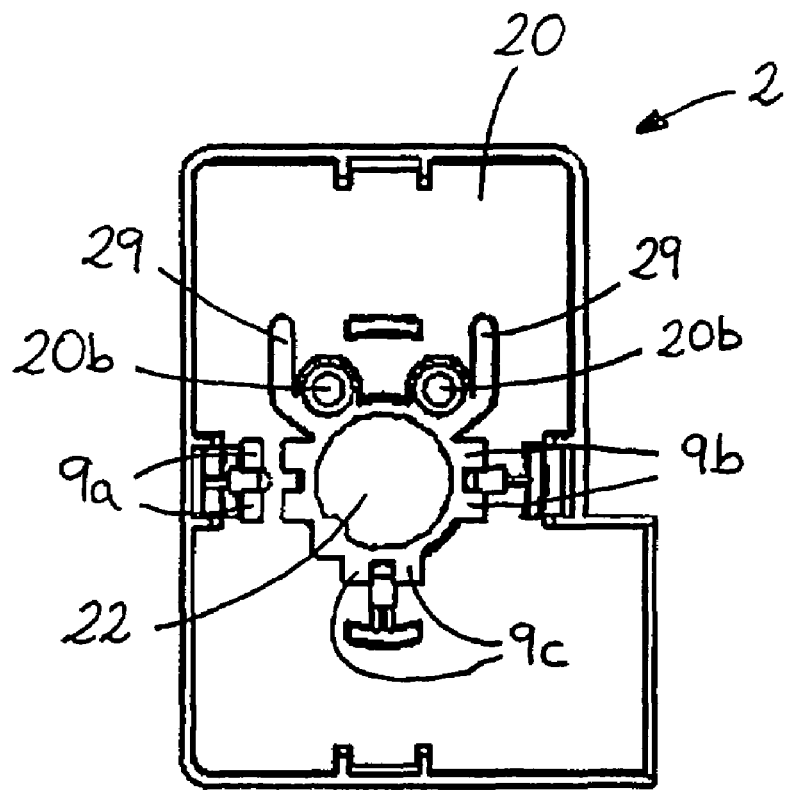
FIG. 6 is a ground view of an embodiment of the body of the device of FIG. 1.
Figure 7:
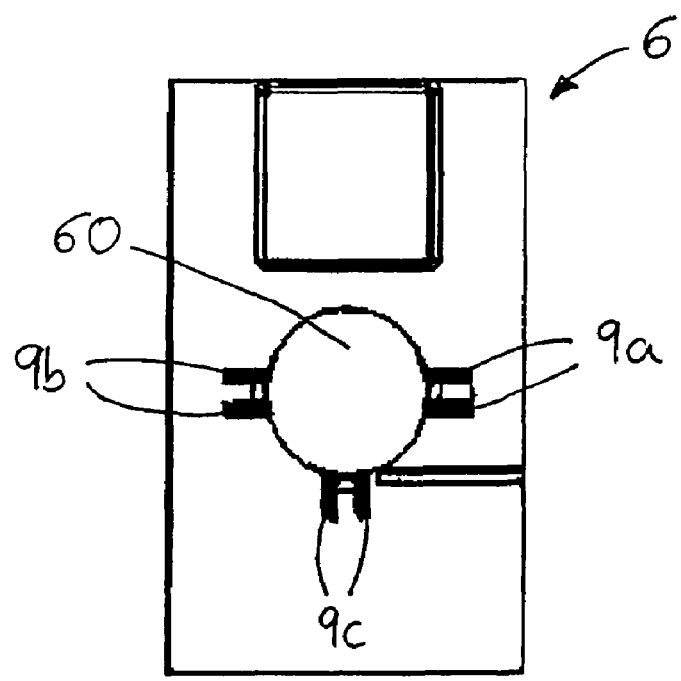
FIG. 7 is a ground view of an embodiment of the cover of the device of FIG. 1.

The device 1 also comprises guidance means preferably disposed on the cover 6, as shown in FIG. 7, in order to focus the light emitted by said light emitter and the light that said light receiver receives, although said guidance means can also be disposed on the body 2 instead of on said cover 6, as shown in FIG. 6. Said guidance means comprise two parallel walls 9a between which is disposed the light emitter, and two parallel walls 9b between which is disposed the light receiver. If said device 1 comprises the second light receiver, said guidance means also comprise two parallel walls 9c between which is disposed said second light receiver.

Figure 8:
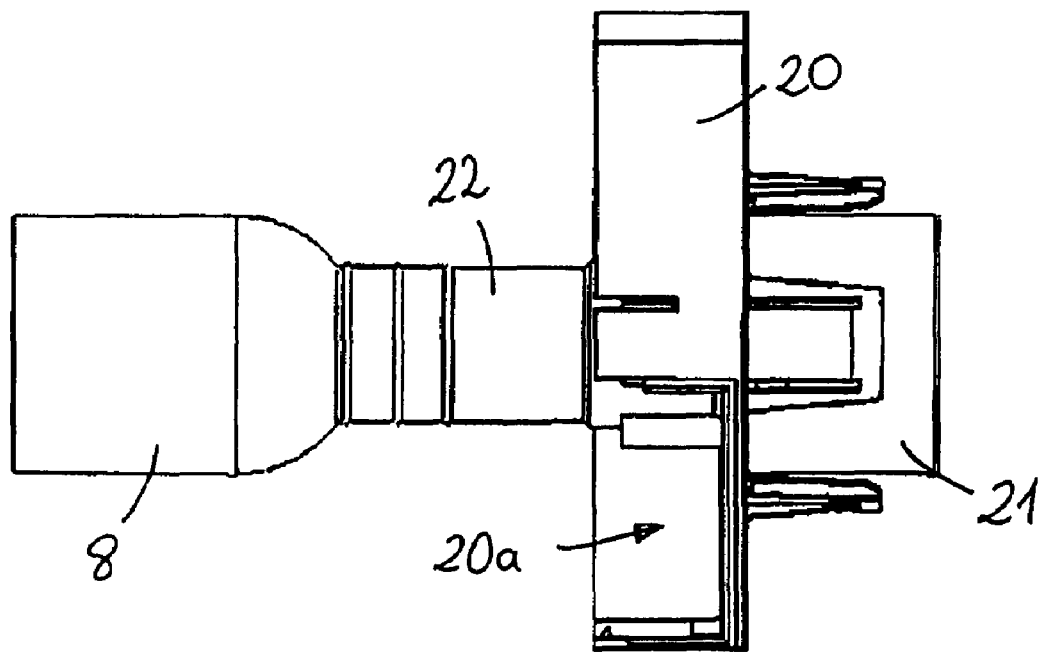
FIG. 8 is a lateral view of the device of FIG. 1, with the mixing conduit connected to said device.

Depending on the location where the device 1 is positioned in the household appliance and whether said device 1 is disposed in series with the fluid whose variables are to be measured, said device 1 can also comprise a mixing conduit 8 that is connected to the outlet conduit 22, as shown in FIG. 8. Said mixing conduit 8 comprises a diameter substantially larger than the diameter of said outlet conduit 22, the fluid that passes through said outlet conduit 22 passing to the mixing conduit 8. In this way, if the fluid that passes through said outlet conduit 22 contains, for example, any type of detergent, due to the diameter, in said mixing conduit 8 said detergent is correctly diluted in said fluid.

Figure 9:
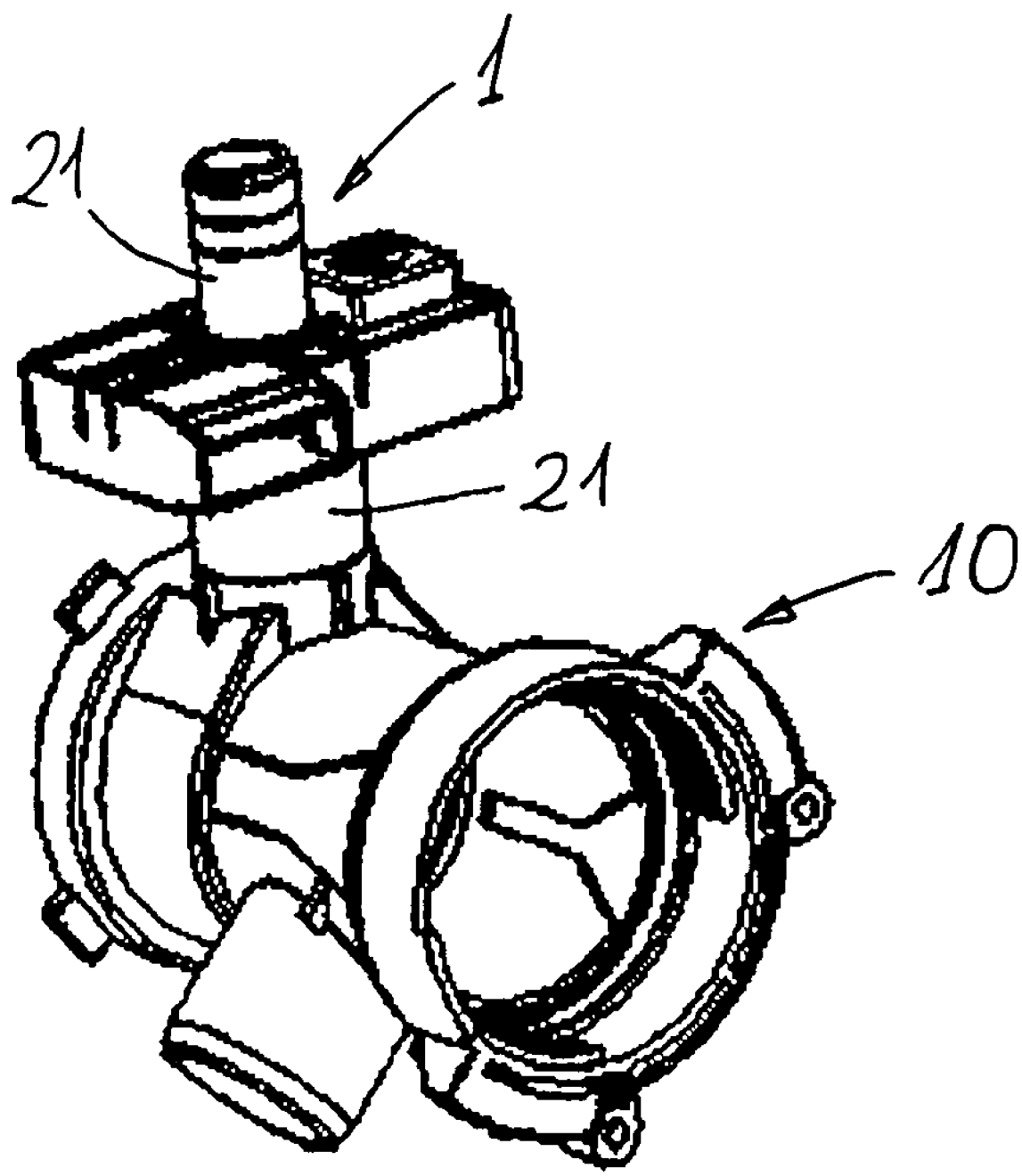
FIG. 9 is a perspective view of the device of FIG. 1 connected to a water pump.

The household appliance comprises at least one water pump 10 for recirculation and/or evacuation, and the device 1 can be integrated in said water pump 10, with said device 1 and said water pump 10 forming a single element, as shown in FIG. 9. This enables the measurement of the variables of the fluid in the required manner, such as in a static regime or a dynamic regime, by disabling or enabling said water pump 10.

The invention claimed is:

1. Sensor device for a household appliance, said device comprising:
   a body,
   detector means to measure at least one variable of a fluid and which comprise a conductivity sensor,
   a printed circuit that receives the variables measured by the detector means, and
   a cover;
   the body comprising:
   a housing where said printed circuit is housed, and
   an inlet conduit and an outlet conduit through which said fluid passes,
   the cover being arranged to close the housing of the body, and said printed circuit and said cover being disposed transversally to said inlet and outlet conduits between said inlet and outlet conduits, the conductivity sensor being connected to the body and connected to or next to said printed circuit.

2. Device according to claim 1, wherein the conductivity sensor comprises two electrodes that are disposed longitudinally and in parallel in one of the inlet or outlet conduits of the body, said electrodes being disposed longitudinal to the flow of the fluid and being connected to the printed circuit.

3. Device according to claim 2, wherein the electrodes are disposed in respective longitudinal grooves of the inlet conduit.

4. Device according to claim 3, wherein the longitudinal grooves comprise respective parallel stoppers, so that the electrodes extend longitudinally to the same length in the inlet conduit.

5. Device according to claim 2, wherein the body of said device comprises fixing means disposed in one of the inlet and outlet conduits, so that the electrodes are disposed in a certain position in relation to the flow of the fluid.

6. Device according to claim 1, wherein the conductivity sensor comprises two inductive conductors rolled up in one of the inlet or outlet conduits, said conductors being next to the printed circuit.

7. Device according to claim 6, wherein the conductors are rolled up in respective ring-shaped grooves of the inlet conduit, with said ring-shaped grooves being parallel and being separated by a certain distance.

8. Device according to claim 7, wherein the ring-shaped grooves are disposed on the outer surface of the inlet conduit, the body comprising insulation means disposed on said inlet conduit and concentric to said inlet conduit, so that said insulation means are disposed on said conductors, thereby insulating said conductors from the exterior.

9. Device according to claim 1, wherein the housing delimits an area around the outlet conduit of the body, the printed circuit being disposed on said area, and said printed circuit and the cover comprising respective cavities that are crossed by said outlet conduit as said printed circuit and said cover are disposed on said area.

10. Device according to claim 1, wherein the detector means comprise a turbidity sensor disposed on the printed circuit to measure the turbidity of the fluid that passes through the outlet conduit, said turbidity sensor comprising a light emitter and at least one light receiver, and the cover comprising guidance means to focus the light emitted by said light emitter and the light received by said light receiver.

11. Device according to claim 1, wherein the detector means comprise a turbidity sensor disposed on the printed circuit to measure the turbidity of the fluid that passes through the outlet conduit, said turbidity sensor comprising a light emitter and at least one light receiver, and the body comprising guidance means to focus the light emitted by said light emitter and the light received by said light receiver.

12. Device according to claim 1, that comprises a mixing conduit connected to the outlet conduit, said mixing conduit comprising a diameter substantially greater than the diameter of said outlet conduit.

13. Device according to claim 1, wherein the household appliance comprises at least one water pump and said device is integrated in said water pump, so that said water pump and said device form a single element.

* * * * *